United States Patent
Takahashi et al.

(10) Patent No.: US 6,178,385 B1
(45) Date of Patent: Jan. 23, 2001

(54) METHOD AND APPARATUS FOR CHECKING THE WRAPPING STATE OF A ROLL

(75) Inventors: Hisashi Takahashi; Toshikazu Ishii; Satoshi Mino; Takayuki Fujiwara; Yoshio Kawakami; Kenji Ozawa, all of Kanagawa (JP)

(73) Assignee: Fuji Photo Film Co., Ltd., Kanagawa-Ken (JP)

(*) Notice: Under 35 U.S.C. 154(b), the term of this patent shall be extended for 0 days.

(21) Appl. No.: 09/220,684

(22) Filed: Dec. 23, 1998

Related U.S. Application Data

(62) Division of application No. 08/607,929, filed on Feb. 28, 1996, now Pat. No. 5,887,076.

(30) Foreign Application Priority Data

Mar. 1, 1995 (JP) .................................................. 7-042036
Mar. 6, 1995 (JP) .................................................. 7-045186

(51) Int. Cl.$^7$ ...................................................... B65B 11/00
(52) U.S. Cl. ............................... 702/41; 702/33; 702/42; 702/43; 53/204; 53/409; 73/862.53
(58) Field of Search .................................. 702/41, 33–36, 702/42, 43, 81, 82, 113–115, 138, 140, 150, 189, 183–185, FOR 130, FOR 123–FOR 126, FOR 135–FOR 137; 364/469.01, 5, 471.01, 472.04, 472.06; 493/37; 53/116–118, 581, 582, 204, 409, 216, 210, 136.2, 214; 162/118, 263; 206/398, 413–416, 316.1, 400, 410; 242/534, 534.1, 534.2, 912, 160.4, 348, 348.1–348.4, 176–178; 73/761, 763, 781, 794–796, 818, 819, 829, 852, 862.49, 862.55, 862.542, 862.635, 862.642, 865.9, 760, 782, 788–790, 811, 813, 862.01, 862.392, 862.53, 858–860; 700/95, 109, 110, 117, 118, 122, 126, 148, 150, 160, 165, 167, 206, 301

(56) References Cited

U.S. PATENT DOCUMENTS

| | | | |
|---|---|---|---|
| 3,354,708 | * 11/1967 | Joron | 73/862.53 |
| 4,033,183 | * 7/1977 | List et al. | 73/862.55 |
| 4,386,707 | 6/1983 | Stube | 209/546 |
| 4,511,044 | * 4/1985 | Connor et al. | 73/862.53 |
| 4,625,493 | * 12/1986 | Yagi et al. | 53/204 |
| 4,679,744 | 7/1987 | Chikamasa et al. | 242/534 |
| 5,206,720 | 4/1993 | Clothiaux et al. | 358/101 |
| 5,359,408 | 10/1994 | Inada et al. | 356/238 |
| 5,592,875 | * 1/1997 | Maschel | 73/862.55 |
| 5,611,500 | * 3/1997 | Smith | 242/534 |

FOREIGN PATENT DOCUMENTS

| | | | |
|---|---|---|---|
| A1 3624419 | 1/1988 | (DE) | B65B/57/00 |
| A2 0330495 | 8/1989 | (EP) | B65B/19/28 |
| A3 0330495 | 8/1989 | (EP) | B65B/19/28 |
| A2 0414265 | 2/1991 | (EP) | G03B/17/26 |
| A3 0414265 | 2/1991 | (EP) | G03B/17/26 |
| 2133873 | 8/1984 | (GB) | G01N/21/90 |

* cited by examiner

*Primary Examiner*—Hal Wachsman
(74) *Attorney, Agent, or Firm*—Sughrue, Mion, Zinn, Macpeak & Seas, PLLC

(57) ABSTRACT

A method of and apparatus for checking a wrapping state of a wrapped roll having end face covers by detecting the force required to press-fit a bushing into a cylindrical core tube and comparing the detected force with a threshold value which is based on the correlation between the force required to press-fit the bushing into the cylindrical core tube and the state of tucking of the end face covers.

10 Claims, 10 Drawing Sheets

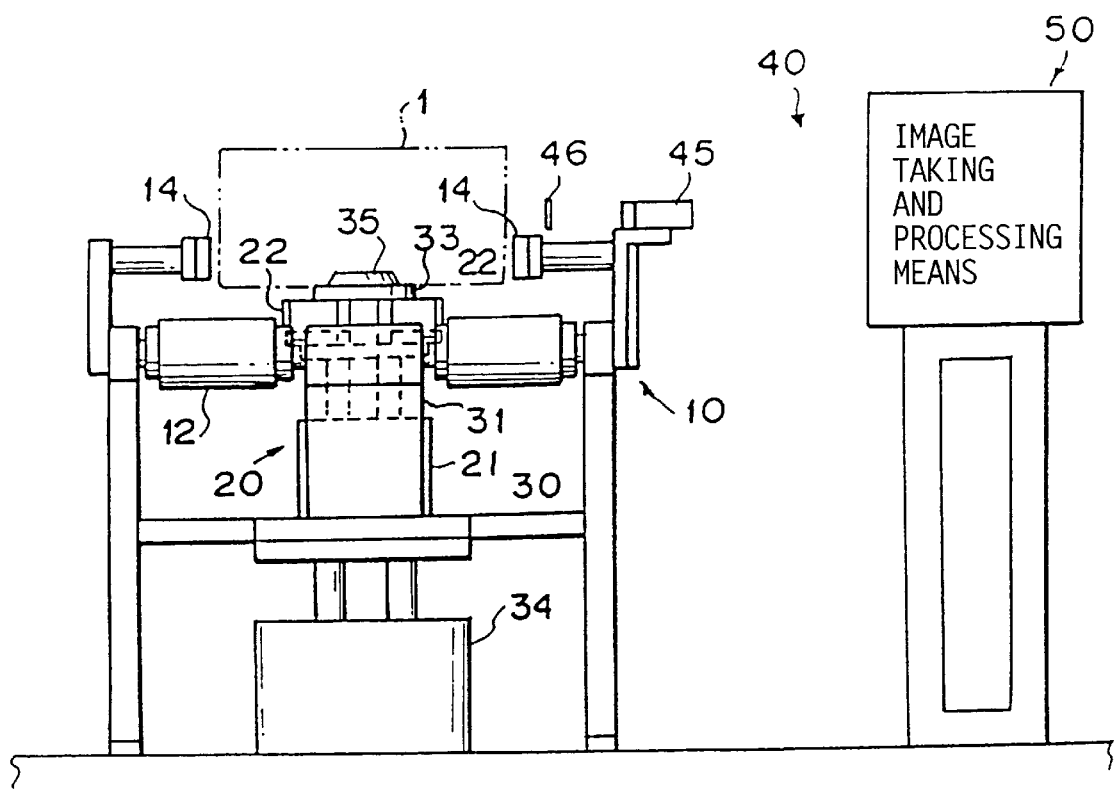
F I G. 5

METHOD AND APPARATUS FOR CHECKING THE WRAPPING STATE OF A ROLL

This is a divisional of application Ser. No. 08/607,929 filed Feb. 28, 1996, which issued into U.S. Pat. No. 5,887,076 the disclosure of which is incorporated herein by reference.

BACKGROUND OF THE INVENTION

1. Field of the Invention

This invention relates to a method of and an apparatus for checking the wrapping state of a wrapped roll of a continuous sheet material which is rolled around a core tube and wrapped with wrapping sheet and the like.

2. Description of the Related Art

There have been known various wrapping materials and wrapping methods for wrapping a roll of sheet material. For example, in one of the known wrapping methods, a leader sheet is bonded to the leading end of the rolled sheet material and an end face cover is bonded to each side edge portion of the leader sheet. The leader sheet is rolled around the sheet roll to cover the side surface of the sheet roll and then the end face covers are folded along the end faces of the roll to cover the end faces and the free edge portion of each end face cover is tucked into the end portion of the core tube. Thereafter a bushing having an outer diameter slightly smaller than the inner diameter of the core tube is press-fitted into each end of the core tube over the tucked portion of the end face cover to fix the cover on the roll.

The wrapping material comprising such a leader sheet and such end face covers is employed, for instance, to wrap a roll of photosensitive material sheet such as photographic film. The wrapping material is so arranged that the outer edges of the bonded area of the leader sheet and the end face covers run along the side edges of the sheet roll and when the leader sheet is pulled, the end face covers are easily torn along the outer edges of the bonded area, whereby the wrapped roll is opened. When the outer edges of the bonded area are not correctly positioned along the side edges of the roll and are on the side surface of the roll, the force required to pull the leader sheet increases and in extreme cases, the end face covers cannot be torn along the outer edges of the bonded area and the leader sheet cannot be properly drawn out.

Further, when the end face covers are not sufficiently bonded to the leader sheet, or the bonded area is blemished, or folding of the end face covers is defective, light-shielding performance and/or water vapor barrier characteristics of the wrapped roll can deteriorate.

Further, when tucking of the end face covers into the core tube is defective, the bushings cannot be fit in the core tube with a sufficient force, which can result in poor light-shielding performance and/or water vapor barrier characteristics of the wrapped roll and/or bushings slipping off during transfer of the wrapped roll.

Especially when the rolled sheet material is photosensitive sheet, the performance of the sheet material deteriorates if the light-shielding performance and/or water vapor barrier characteristics of the wrapped roll are poor. For example, a roll of photosensitive sheet material wrapped in a dark room will be exposed to light as soon as it is transferred to a light room. Accordingly if a defect in wrapping state is found in a dark room, the roll must be rewrapped before transferring to a light room.

However, there has not been developed an apparatus for automatically checking the wrapping state of a wrapped roll and conventionally wrapping state has been visually checked. Such a method of checking wrapping state of the rolled sheet is disadvantageous in that it takes a large amount of labor to visually check a large number of rolls and reliability of the check is poor.

SUMMARY OF THE INVENTION

In view of the foregoing observations and description, the primary object of the present invention is to provide a method of and an apparatus for automatically checking wrapping state of a wrapped roll.

Another object of the present invention is to provide a method of and an apparatus for automatically checking tucking of the end face covers into the core tube.

In accordance with a first aspect of the present invention, an image of a wrapped roll placed in a predetermined position is taken by an image taking means, information on the image of the wrapped roll is processed with respect to the density of the image and data on wrapping state of the wrapped roll is detected by a detecting means, and whether the wrapping state of the wrapped roll is satisfactory is determined on the basis of the detected data by a determining means.

In one embodiment, the wrapped roll comprises a rolled sheet material wrapped with a wrapping member including a leader sheet which is substantially equal to the rolled sheet material in width and is bonded to the leading end of the rolled sheet material and end face covers are bonded to opposite side edge portions of the leader sheet, the leader sheet being rolled around the rolled sheet material to cover the side surface of the sheet roll and the end face covers being folded along the end faces of the rolled sheet material to cover the end faces, the image taking means takes an image of the bonded area of the leader sheet and the end face covers on the side surface of the wrapped roll and a portion around the bonded area, and whether the wrapping state of the wrapped roll is satisfactory is determined on the basis of the position of the edge of the bonded area relative to the rolled sheet material and/or the state of adhesion between the leader sheet and the end face covers. The expression "the state of adhesion between the leader sheet and the end face covers" means, for instance, whether the adhesion between the leader sheet and the end face covers is good and/or whether the bonded area is blemished.

For example, the detecting means detects the position of the edge of the bonded area by binary-coding the information on the image of the bonded area of the leader sheet and the end face covers and the portion around the bonded area with respect to the density of image, adding the binary-coded image densities for the respective picture elements in the circumferential direction of the wrapped roll and comparing each of the sums obtained with a predetermined threshold value. The determining means determines the accuracy of positioning of the edge of the bonded area by comparing the position of the edge of the bonded area detected by the detecting means with a predetermined reference position.

The wrapped roll may be supported for revolution about its longitudinal axis by a rotary support means and the image taking means may be fixed in a position where it can take an image of the outer peripheral surface of the wrapped roll which is revolved by the rotary support means.

Thus in accordance with the first aspect of the present invention, the wrapping state of a wrapped roll is automatically checked according to the density of the image of the wrapped roll.

Further, when the position of the edge of the bonded area is detected by binary-coding the information on the image of the bonded area of the leader sheet and the end face covers and the portion around the bonded area with respect to the density of image, adding the binary-coded image densities for the respective picture elements in the circumferential direction of the wrapped roll and comparing each of the sums obtained with a predetermined threshold value, the position of the edge of the bonded area can be easily detected with a high accuracy, whereby accuracy of positioning of the edge of the bonded area can be surely determined.

When the wrapped roll is revolved with the image taking means fixed, the apparatus can be simpler in structure as compared to when the image taking means is moved with the wrapped roll fixed.

In accordance with a second aspect of the present invention, there is provided a method of checking the wrapping state of a wrapped roll comprising a rolled sheet material which is rolled around a cylindrical core tube, end face covers which cover opposite end faces of the rolled sheet material and part of which is tucked into the core tube, and a bushing which has an outer diameter slightly smaller than the inner diameter of the core tube and is press-fitted into each end of the core tube over the tucked portion of the end face cover. The method of the second aspect of the present invention is characterized in that whether tucking of the end face cover into the core tube is satisfactory is determined by detecting the force required to press-fit the bushing in the core tube and comparing the detected force with a threshold value which is determined on the basis of a correlation between the force required to press-fit the bushing into the core tube and the state (satisfactory or unsatisfactory) of tucking of the end face cover.

Since the force required to press-fit the bushing depends not only on the state of tucking but also on the outer diameter of the bushing, the inner diameter of the core tube and the like, almost all the factors which can affect the fitting force of the bushing, light-shielding performance and water vapor barrier characteristics of the wrapped roll can be checked by checking the force required to press-fit the bushing in the core tube.

Our investigation reveals that there is a deep correlation between the state of tucking of the end face cover and the force required to press-fit the bushing in the core tube. That is, when the force required to press-fit the bushing in the core tube is larger than a predetermined threshold value, it may be determined that the tucking of the end face cover is satisfactory and vice versa.

The method in accordance with the second aspect of the present invention may be carried out, for instance, by an apparatus comprising a press-fitting means for press-fitting the bushing in the core tube, a press-fitting force detecting means which detects the press-fitting force transmitted to the press-fitting means from the bushing when press-fitting the bushing in the core tube and a determining means which compares the press-fitting force with a predetermined threshold value and determines whether the tucking of the end face cover is satisfactory.

BRIEF DESCRIPTION OF THE DRAWINGS

FIG. 5 is a right side view of the apparatus.

DESCRIPTION OF THE PREFERRED EMBODIMENT

Figure 1:
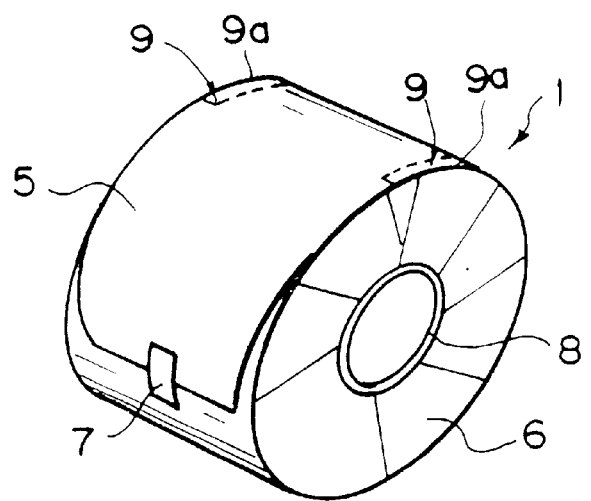
FIG. 1 is a perspective view of an example of a wrapped roll.
Figure 2:
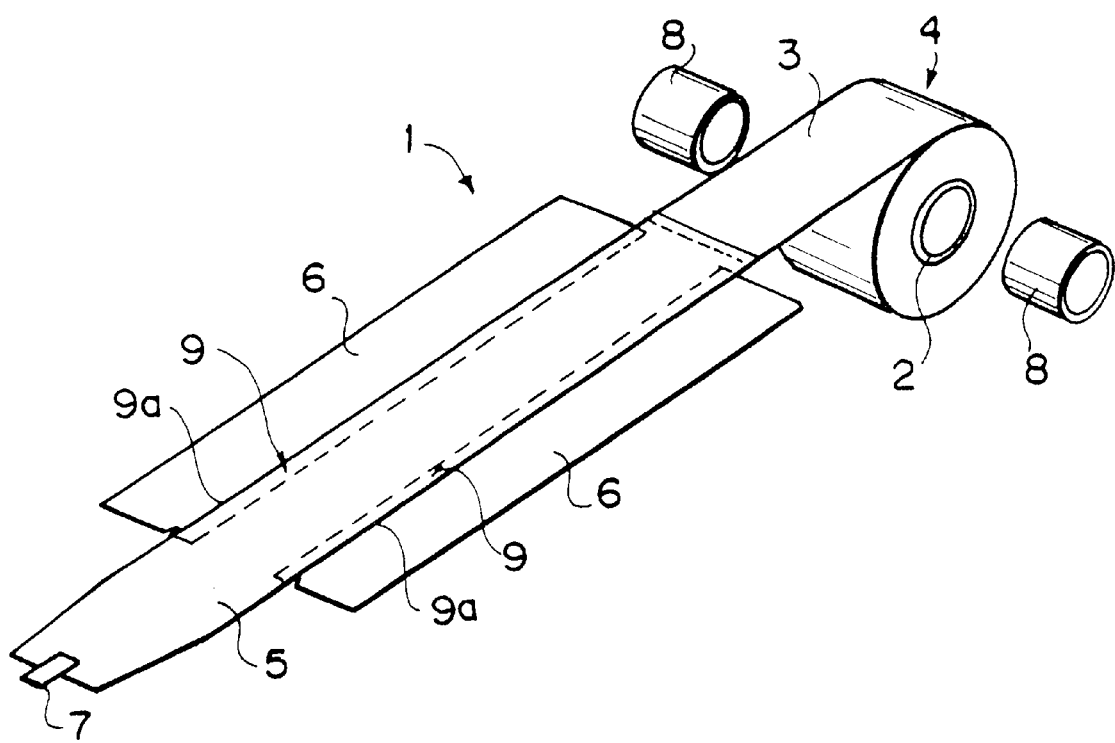
FIG. 2 is an exploded perspective view of the wrapped roll.

In FIGS. 1 and 2, a wrapped roll 1 comprises a roll 4 of photosensitive sheet material 3 rolled around a cylindrical core tube 2, a leader sheet 5 connected to the leading end of the sheet material 3 and a pair of end face covers 6 respectively bonded to opposite side edges of the leader sheet 5 at their one side edges.

The leader sheet 5 is formed of moisture-proof and light-shielding material and is rolled around core tube 2 over the sheet material roll 4 to cover the outer peripheral surface of the roll 4. The leading end of the leader sheet 5 is fixed by an adhesive tape 7. When the leader sheet 5 is properly rolled around the sheet material roll 4, the outer edge 9a of each bonded area 9 of the leader tape 5 and the end face cover 6 is substantially aligned with the edge of the roll 4 between the side surface and the end face of the roll 4.

The end face cover 6 is folded along the end face of the roll 4 to cover the end face and the free edge portion of the end face cover 6 is tucked into the core tube 2. The end face cover 6 is fixed by press-fitting a bushing 8 having an outer diameter slightly smaller than the inner diameter of the core tube 2 into the core tube 2 over the tucked portion of the end face cover 6.

The sheet material roll 4 is wrapped in the manner described above in a dark room and shipped as a wrapped roll 1. The wrapped roll 1 is installed on a machine using the sheet material roll 4 in a light room. When the leader sheet 5 is pulled out after installing the wrapped roll 1 on the machine, the end face covers 6 are torn along the outer edges 9a of the bonded area 9 and the wrapped roll 1 is opened.

Whether the outer edges 9a of the bonded areas 9 are positioned in place is checked by a wrapping state checking apparatus in accordance with a first embodiment of the present invention shown in FIGS. 3 to 6.

As shown in FIGS. 3 to 6, the checking apparatus of this embodiment comprises a transfer means 10 which transfers the wrapped roll 1, a locator means 20 which positions the wrapped roll 1 in a predetermined position, a rotary support means 30 which supports the wrapped roll 1 for revolution about the longitudinal axis of the roll 1, an image taking means 40 which takes an image of the bonded areas 9 of the leader sheet 5 and the end face covers 6 on the side surface of the wrapped roll 1 and a portion around the bonded areas 9, and an image processing means 50 which processes information on the image taken by the image taking means 40 with respect to the density of the image and checks the accuracy of positioning of the outer edges 9a of the bonded areas 9.

Figure 3:
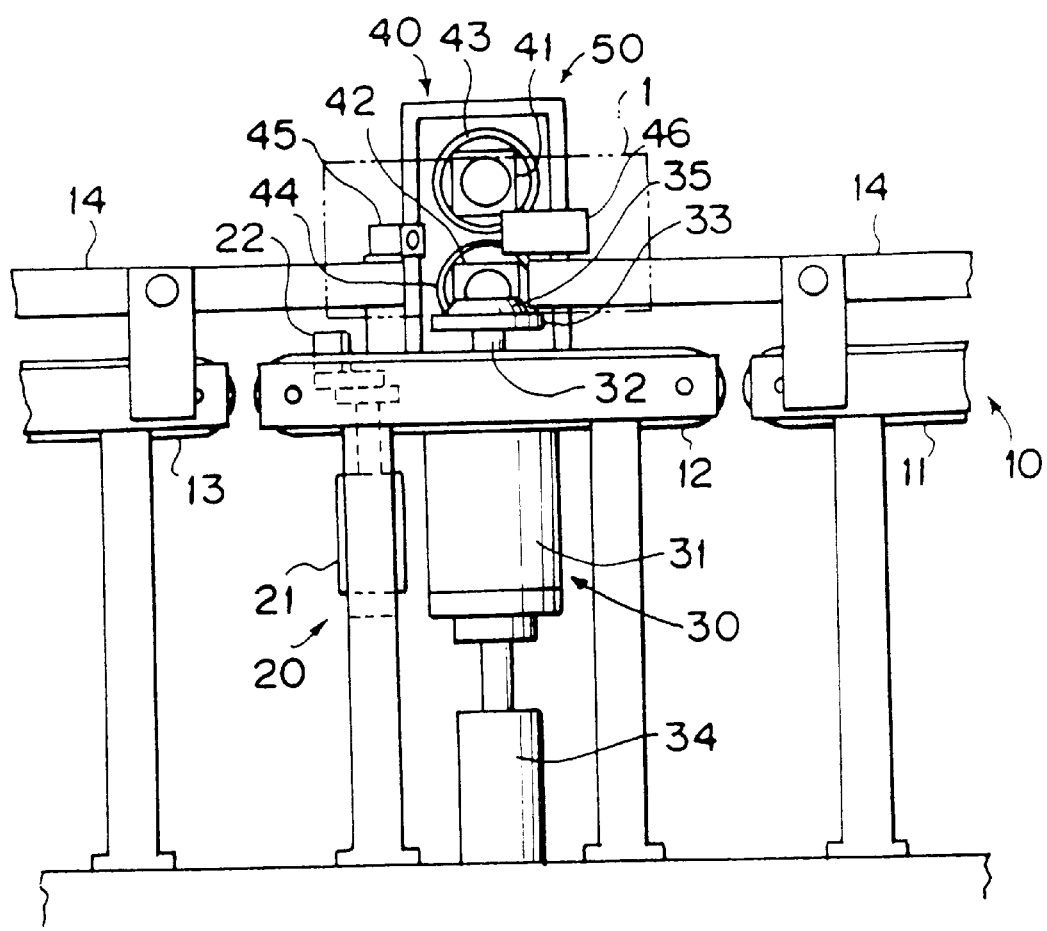
FIG. 3 is a front view of a wrapping state checking apparatus in accordance with a first embodiment of the present invention.
Figure 4:
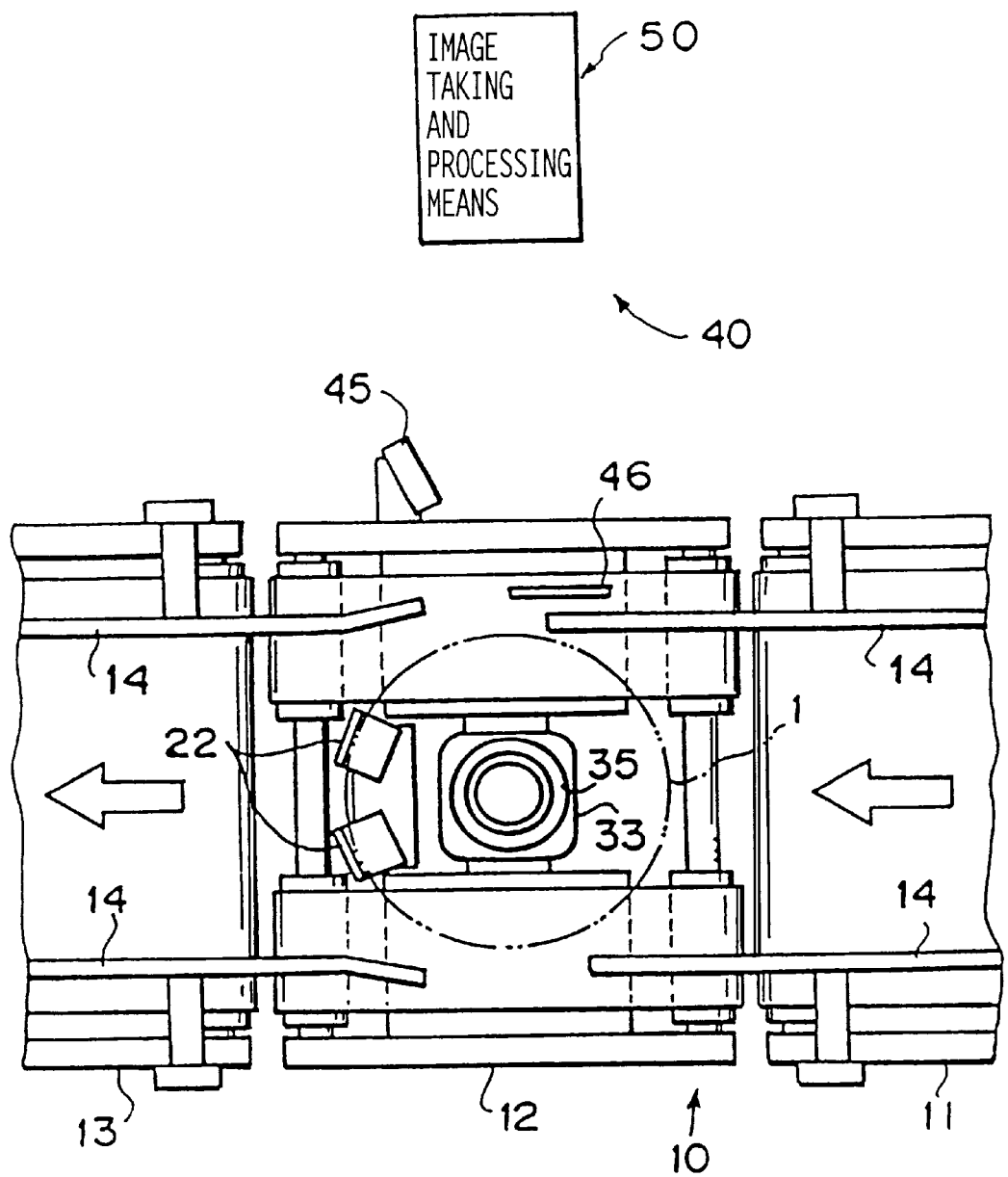
FIG. 4 is a plan view of the apparatus.
Figure 6:
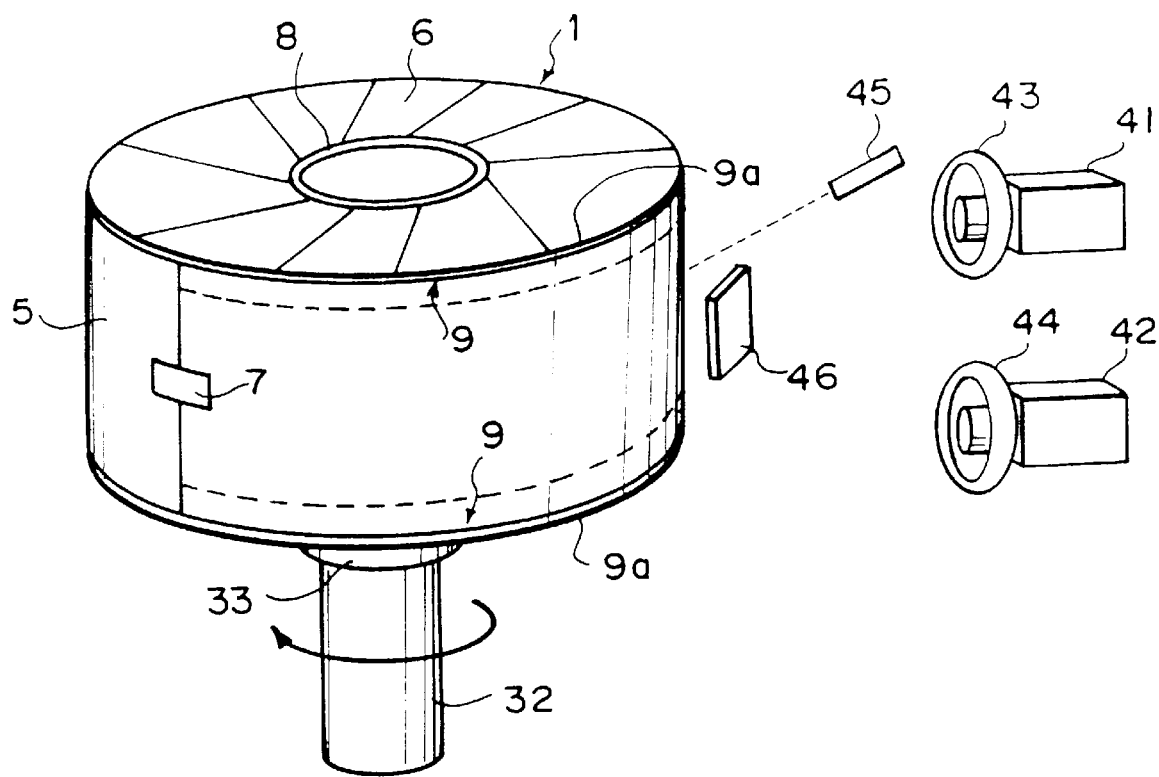
FIG. 6 is a fragmentary perspective view of the apparatus.

The transfer means 10 comprises an upstream side conveyor 11, and an intermediate conveyor 12 (FIG. 4), a downstream side conveyor 13 and a conveyor guide 14 and transfers the wrapped roll from upstream to downstream (from right to left in FIGS. 3 and 4). The locator means 20 comprises a cylinder 21 movable up and down and a stopper 22 provided on the top of the cylinder 21. The rotary support means 30 comprises a motor 31 with reduction gears, a table 33 mounted on the end of an output shaft 32 of the motor 31, and a cylinder 34 which supports the motor 31 and the table 33 to be movable up and down. A tapered portion 35 which is inserted into the bushing 8 of the wrapped roll 1 is provided on the upper surface of the table 33.

The image taking means 40 comprises first and second cameras 41 and 42 which may be, for instance, CCD cameras, ring illuminators 43 and 44 respectively disposed to surround the first and second cameras 41 and 42 and an end sensor 45 which detects the leading end of the leader sheet 5. The image processing means 50 comprises a detecting means (not shown) which detects the outer edges 9a of the bonded area 9 by an image processing to be described later and a determining means (not shown) which determines the accuracy of positioning of the detected outer edges 9a of the bonded areas 9.

The procedure of checking the wrapping state of the wrapped roll 1 by the checking apparatus of this embodiment will be described, hereinbelow.

First a wrapped roll 1 is conveyed from the upstream side by the upstream side conveyor 11 and is transferred to the intermediate conveyor 12. At this time, the table 33 is positioned below the surface of the intermediate conveyor 12 and the stopper 22 is on the surface of the intermediate conveyor 12. When the wrapped roll 1 is brought into abutment against the stopper 22, the intermediate conveyor 12 is stopped and the cylinder 21 is moved downward to lower the stopper 22 below the surface of the intermediate conveyor 12.

Then the table 33 is moved upward by the cylinder 34 and the tapered portion 35 on the table 33, which has an outer diameter slightly smaller than the inner diameter of the bushing 8, is inserted into the bushing 8, whereby the wrapped roll 1 is positioned with a high accuracy. Thereafter the motor 31 drives the table 33 to revolve the wrapped roll 1 about the longitudinal axis thereof.

Figure 7:
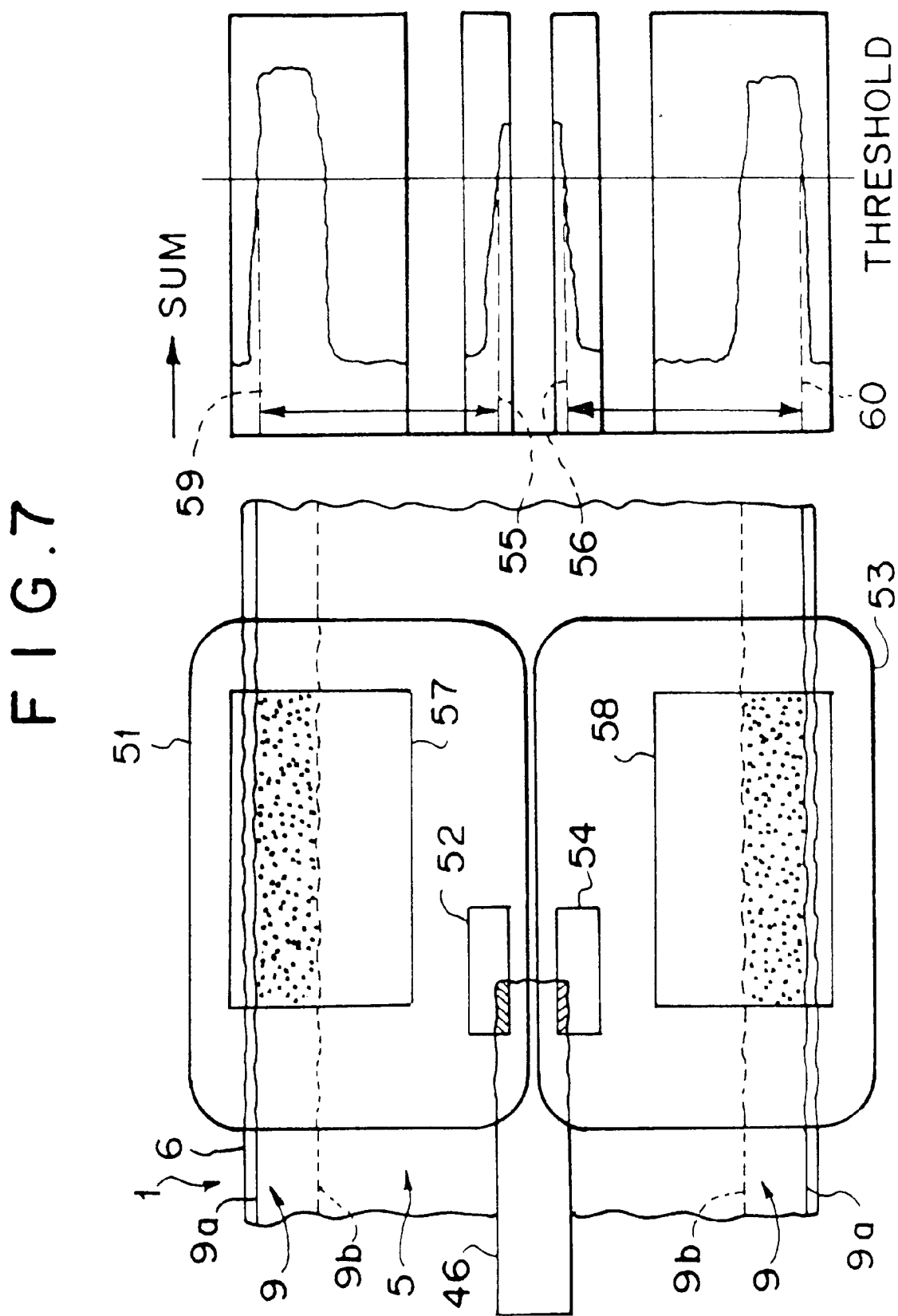
FIG. 7 is a view for illustrating image taking and image processing.
Figure 8:
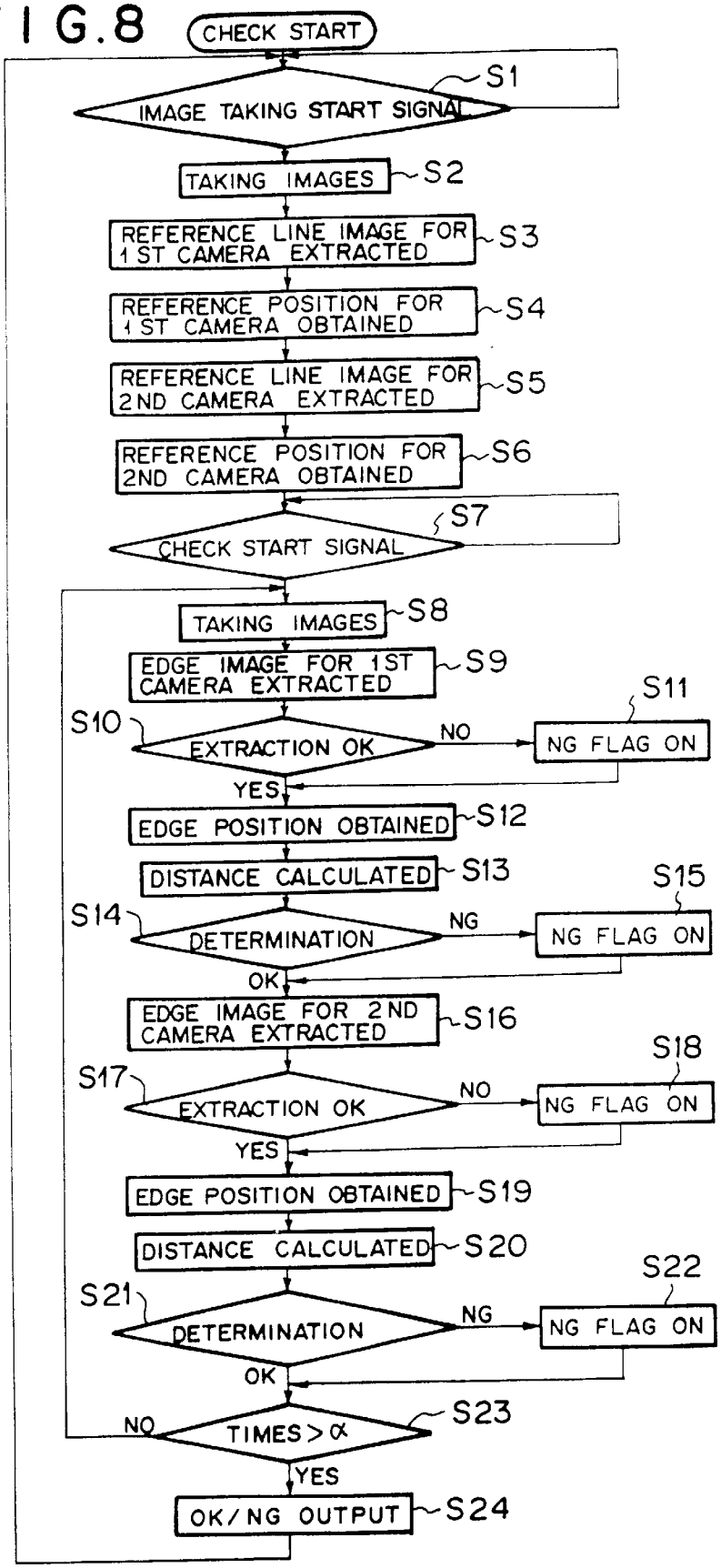
FIG. 8 is a flow chart for illustrating procedure of image taking and image processing.

After the wrapped roll. 1 begins to revolve, the image taking means 40 takes an image of the bonded areas 9 and a portion around the bonded areas 9 and the image processing means 50 processes the image information and determines the accuracy of positioning of the detected outer edges 9a of the bonded areas 9 according to the procedure shown in FIGS. 7 and 8.

A reference plate 46 is disposed between the first and second cameras 41 and 42 and the wrapped roll 1 on the table 33. As will become apparent later, the reference plate 46 provides reference lines on the basis of which the positions of the outer edges 9a of the bonded areas 9 are measured so that the positions of the outer edges 9a of the bonded areas 9 can be measured without being affected by the positions of the cameras 41 and 42 relative to the table 33. With reference to FIGS. 7 and 8, when a reference plate image taking start signal is output, the first and second cameras 41 and 42 simultaneously take images of the wrapped roll 1. (steps S1 and S2 in FIG. 8) The illuminators 43 and 44 emit light in synchronization with image taking by the cameras 41 and 42.

When image information is taken, the detecting means of the image processing means 50 extracts an image of the reference line for the first camera 41 (step S3) and reference position 55 (FIG. 7) for the first camera 41 is obtained. (step S4) The reference position 55 is obtained by binary-coding the image density of image information on the upper edge of the reference plate 46 and a portion therearound taken in a reference plate image processing window 52 set in the image region 51 of the first camera 41 as shown in FIG. 7, adding the binary-coded image densities for the respective picture elements in the window 52 in the circumferential direction (in the horizontal direction as seen in FIG. 5) of the wrapped roll 1 and comparing each of the sums obtained with a predetermined threshold value.

In a similar manner, an image of the reference line for the second camera 42 is extracted (step S5) and reference position 56 for the second camera 42 is obtained. (step S6) In FIG. 7, reference numerals 53 and 54 respectively denote the image region of the second camera 42 and a reference plate image processing window set in the image region 53.

When the end sensor 45 detects the leading end of the leader sheet 5 of the wrapped roll 1, the end sensor 45 outputs a check start signal representing that the image of the bonded areas 9 and portions therearound is to be taken. The end sensor 45 may be a supersonic sensor which detects the leading end of the leader sheet 5 as a difference in level or may be a color sensor, a mark sensor or the like which detects the adhesive tape 7 on the leading end of the leader sheet 5.

Then when the check start signal is output, the first and second cameras 41 and 42 simultaneously take images of the bonded areas 9 and portions therearound. (steps S7 and S8)

When image information on the bonded areas 9 and portions therearound is taken, the detecting means of the image processing means 50 extracts an image of the outer edge 9a of the bonded area 9 in the image region 51 of the first camera 41 (step S9) and position 59 of the outer edge 9a is obtained. (steps S10 and S12) The position 59 of the outer edge 9a is obtained by binary-coding the image density of image information on the bonded area 9 and a portion therearound taken in a bonded area image processing window 57 set in the image region 51 of the first camera 41 as shown in FIG. 7, adding the binary-coded image densities for the respective picture elements in the window 57 in the circumferential direction of the wrapped roll 1 and comparing each of the sums obtained with a predetermined threshold value.

When the position 59 of the outer edge is obtained, the determining means of the image processing means 50 calculates the distance between the reference position 55 for the first camera 41 and the position 59 of the outer edge 9a. (step S13) The determining means determines whether the accuracy in positioning the outer edge 9a is satisfactory on the basis of whether the calculated distance between the reference position 55 for the first camera 41 and the position 59 of the outer edge 9a is within a predetermined range. (step S14) When the determining means determines that the accuracy in positioning the outer edge 9a is not satisfactory, the determining means sets an NG flag. (step S15) Further, the determining means sets an NG flag also when an image of the outer edge 9a of the bonded area 9 cannot be extracted. (step S11)

In a similar manner, an image of the outer edge 9a of the bonded area 9 in the image region 53 of the second camera 42 is extracted (step S16), position 60 of the outer edge 9a is obtained (step S19), the distance between the reference position 56 and the position 60 of the outer edge 9a is calculated (step S20) and whether the accuracy in positioning the outer edge 9a is satisfactory is determined (step S21).

When it is determined that the accuracy in positioning the outer edge 9a is not satisfactory or when an image of the outer edge 9a of the bonded area 9 cannot be extracted, an NG flag is set. (step S22 or S18) In FIG. 7, reference numeral 58 denotes the bonded area image processing window set in the image region 53 of the second camera 42.

These checking steps are performed a predetermined number of times to cover the entire area of the outer surface of the wrapped roll 1, and then whether the accuracy in positioning the outer edge 9a is satisfactory is collectively determined on the basis of whether or not there is an NG flag or a number of NG flags. The result of determination is output to an operator or the like. (steps S23 and S24)

After the checking is ended, the motor 31 is stopped, the table 33 is moved downward and the intermediate conveyor 12 transfers the wrapped roll 1 to the downstream side conveyor 13. After the wrapped roll 1 is transferred to the downstream side conveyor 13, the stopper 22 is moved upward and the wrapped roll 1 is conveyed downstream.

When the table 31 is inclined, the level of the wrapped roll 1 fluctuates during revolution. In order to avoid this, an angle detecting means such as an encoder may be provided on the output shaft 32 of the motor 31, thereby locating the table 33 in the same position each time.

Though the wrapping state checking apparatus of the first embodiment described above is for checking the accuracy in positioning the outer edges 9a of bonded areas 9, the wrapping state checking apparatus can be modified to check whether the adhesion between the leader sheet and the end face covers is good, whether the bonded area is blemished or whether tucking of the end face covers into the core tube is good by changing the image processing.

A wrapping state checking apparatus in accordance with a second embodiment of the present invention will be described with reference to FIGS. 9 to 11, hereinbelow.

Figure 9:
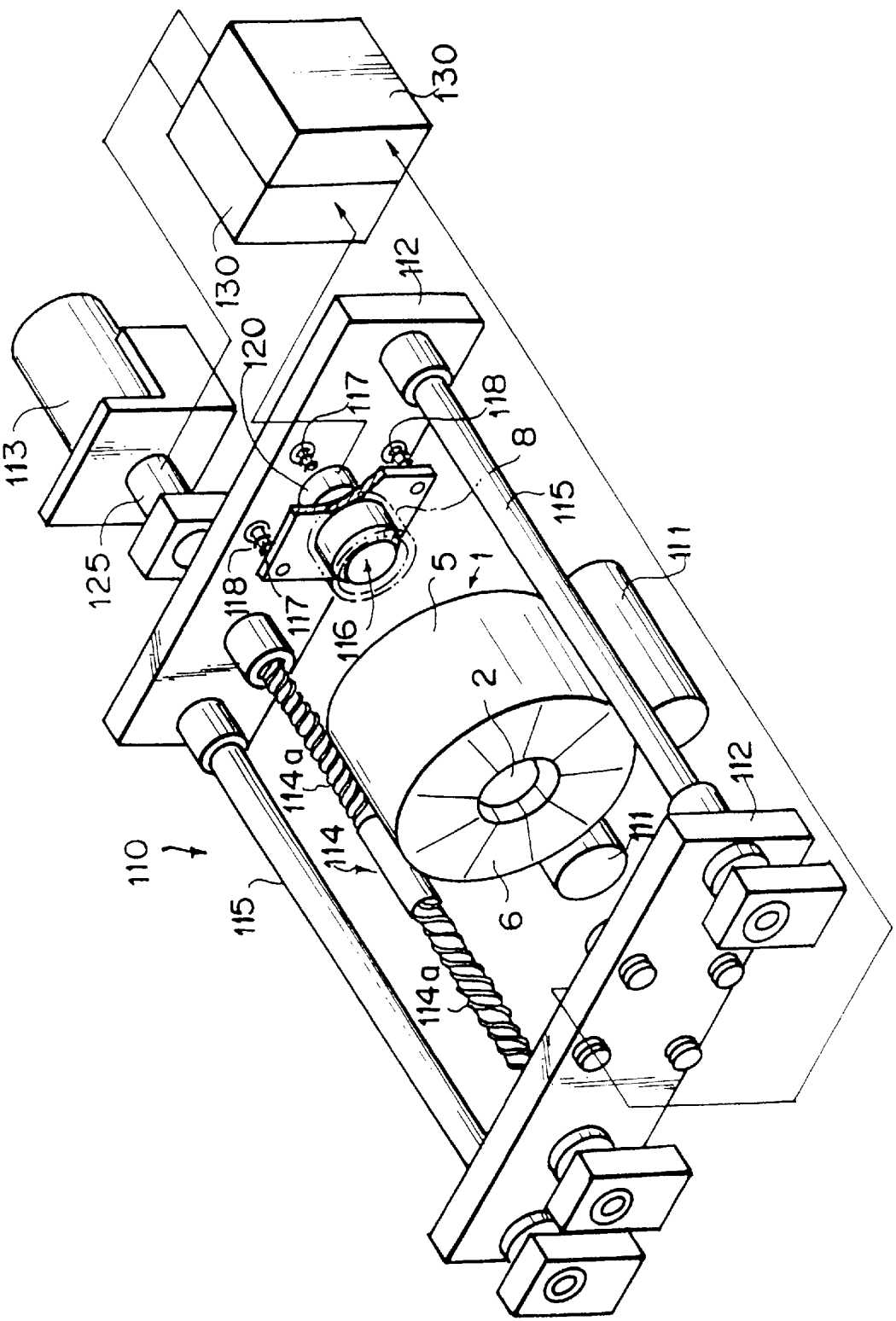
FIG. 9 is a front view of a wrapping state checking apparatus in accordance with a second embodiment of the present invention.
Figure 10:
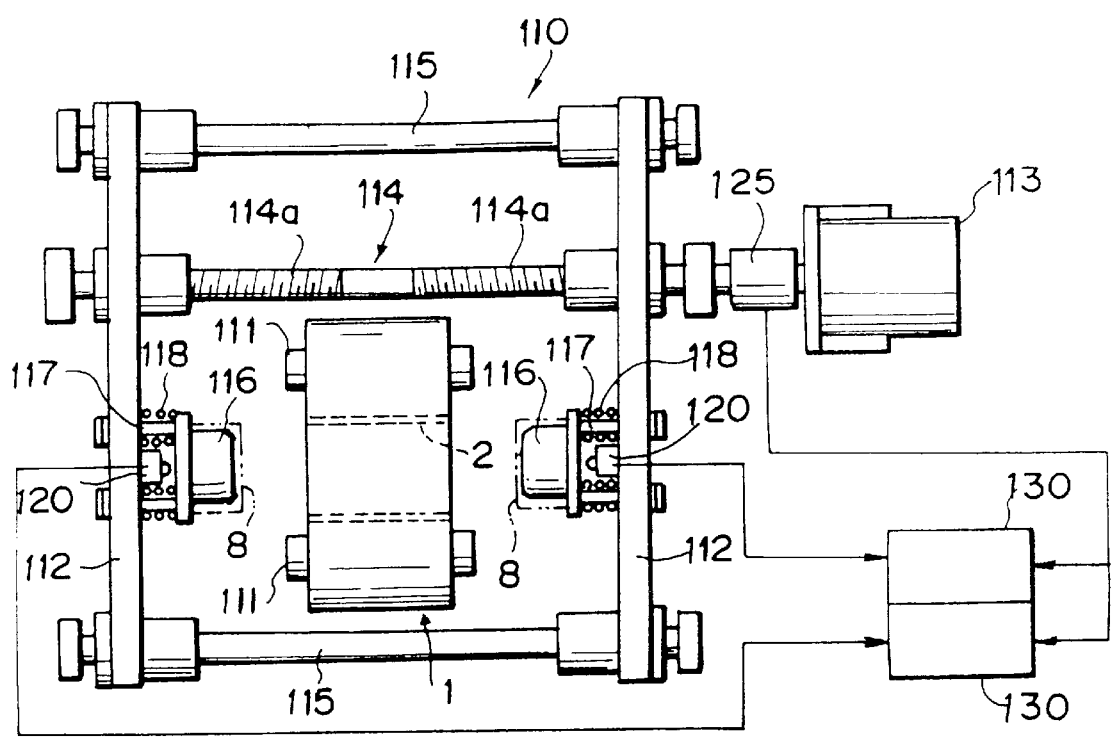
FIG. 10 is a plan view of the apparatus.

In FIGS. 9 and 10, the wrapping state checking apparatus of this embodiment is shown for checking tucking of the end face covers 6 into the core tube 2 of the wrapped roll 1 shown in FIGS. 1 and 2, and comprises a press-fitting means 110 which press-fits bushings 8 in the core tube 2 of the wrapped roll 1, load cells 120 each for detecting the force required to press-fit the bushing 8 in the core tube 2, and comparators 130 which compare the force detected by the respective load cells 120 with a predetermined threshold value and determines whether the tucking of the end face covers 6 into the core tube 2 is satisfactory.

The press-fitting means 110 comprises a support 111 for supporting the wrapped roll 1 in a predetermined position, a pair of movable plates 112 which are disposed in parallel to each other on opposite sides of the support 111 and a motor 113 for driving the plates 112. The output shaft of the motor 113 is connected to a drive shaft 114. The left and right end portions of the drive shaft 114 are threaded (114a) in opposite directions and are engaged with internal threads formed in the respective movable plates 112 so that when the drive shaft 114 is revolved in one direction by the motor 113, the plates 112 are moved toward each other along a pair of guide rods 115 and when the drive shaft 114 is revolved in the other direction, the plates 112 are moved away from each other along the guide rods 115.

A chuck 116 for holding the bushing 8 is provided on the inner surface of each plate 112. The chuck 116 is supported on a rod 117 fixed to the movable plate 112 and is slightly movable along the rod 117 toward the plate 112. The chuck 116 is urged away from the plate 112 by a coiled spring 118 mounted on the rod 117 and when the bushing 8 is press-fitted in the core tube 2, the chuck 116 is moved toward the plate 112 compressing the coiled spring 118 under the force transmitted from the bushing 8.

The load cell 120 is disposed between the movable plate 112 and the chuck 116 and outputs an electric voltage proportional to the magnitude of the force transmitted to the chuck 116 during press-fitting. The output of the load cell 120 is input into the comparator 130.

A threshold voltage which has been set according to the relation between the state of tucking of the end face cover 6 into the core tube 2 and the force transmitted to the chuck 116 from the bushing 8 when press-fitting the bushing 8 into the core tube 2 is stored in the comparator 130. The manner of setting the threshold voltage will be described with reference to FIG. 11, hereinbelow. FIG. 11 shows an example of the relation between the output voltage of the load cell 120 and the amount of insertion of the bushing 8 when the tucking of the end face cover 6 is satisfactory.

Figure 11:
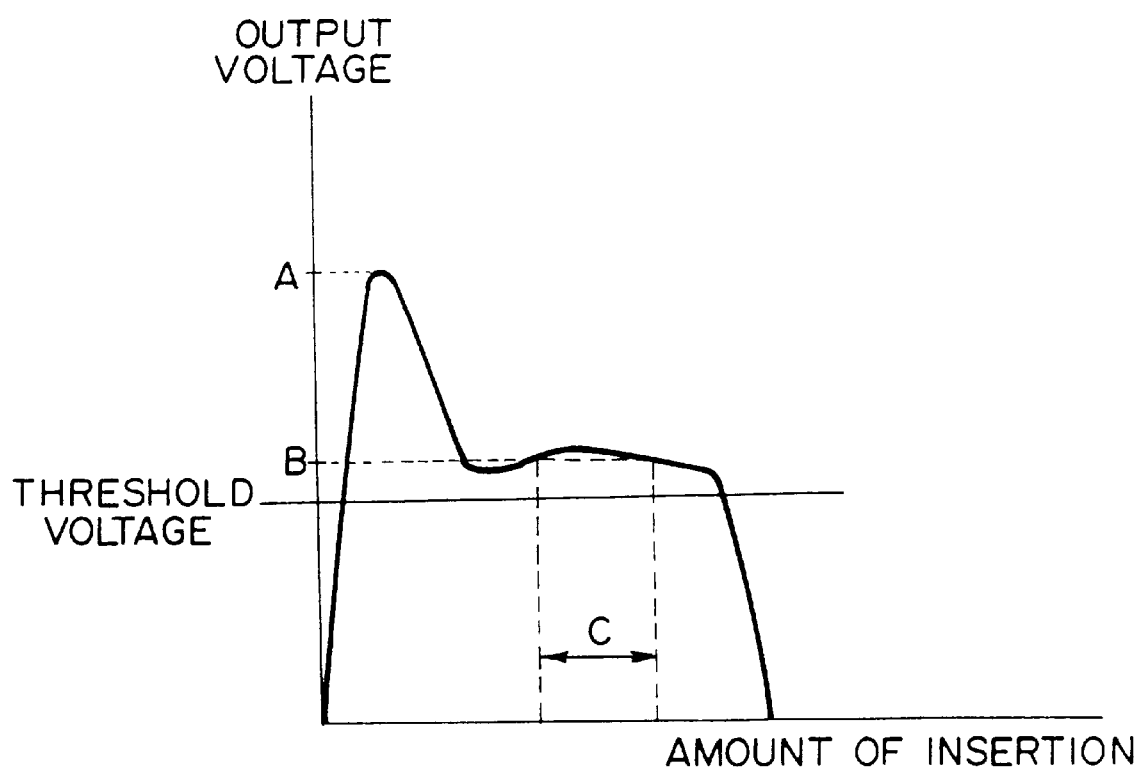
FIG. 11 is a view showing an example of the relation between the output voltage of the load cell and the amount of insertion of the bushing into the core tube.

As shown in FIG. 11, the output voltage of the load cell 120 takes a peak value A just after start of press-fitting and then lowers and settles to a value B until end of press-fitting. The value A is greatly affected by the position of the chuck 116 relative to the core tube 2. On the other hand, the value B is closely related to the state of tucking and less affected by the position of the chuck 116 relative to the core tube 2. That is, the output voltage of the load cell 120 settles to the value B when tucking of the end face cover 6 is satisfactory, while the output voltage of the load cell 120 settles to a value substantially lower than the value B when tucking of the end face cover 6 is unsatisfactory.

Thus in this embodiment, the threshold voltage is set to be compared with the output voltage of the load cell 120 at the time the output voltage of the load cell 120 settles. Further as shown in FIGS. 9 and 10, the output shaft of the drive motor 113 is provided with an encoder 125 which outputs a signal representing the time range in which the output voltage of the load cell 120 settles (the time indicated at C in FIG. 11), and the comparators 130 compare the output voltages of the load cells 120 with the threshold voltage only in the time range C.

The procedure of checking the state of tucking with the checking apparatus of this embodiment will be described, hereinbelow.

First a wrapped roll 1 is placed on the support 111. Then the bushings 8 are set on the chucks 116 and the drive motor 113 is operated to move the movable plates 112 toward each other. When the bushings 8 begin to be inserted into the core tube 2, the load cells 120 detect the forces transmitted to the respective chucks 116 from the bushings 8 and the outputs of the load cells 120 are input into the respective comparators 130.

Each comparator 130 receives the signal representing the time range in which the output voltage of the load cell 120 settles from the encoder 125 and compares the output voltage of the load cell 120 with the threshold voltage only in the time range. When the output voltage of the load cell 120 is not lower than the threshold voltage, the comparator 130 determines that the tucking of the end face is good and vice versa.

Thus in accordance with this embodiment, the state of tucking of the end face cover can be checked even in a dark room on the basis of the force required to press-fit the bushing which is an objective value.

Though, in the embodiments described above, the wrapped roll is a roll of photosensitive sheet, the present invention may be applied to various wrapped rolls other than a roll of photosensitive sheet.

In accordance with the present invention, as can be understood from the description above, a check of the wrapping state of a wrapped roll which has been performed by visual inspection is automatically performed and accordingly the reliability of the check is improved and manpower is saved. Further collection of quantitative data is facilitated and such data can be used for process control and/or analysis of trouble.

What is claimed is:

1. A method of checking a wrapping state of a wrapped roll, the wrapped roll having a cylindrical core tube with sheet material rolled around the cylindrical core tube and end face covers which cover respective opposite end faces of the rolled sheet material, and wherein portions of the end face covers are tucked into the cylindrical core tube; said method comprising the steps of:

press-fitting bushings, having outer diameters smaller than an inner diameter of the cylindrical core tube, in the cylindrical core tube over the tucked portions of the end face covers, respectively, and detecting a force required to press-fit the bushings in the cylindrical core tube and comparing the detected force with a threshold value which is determined on the basis of a correlation between the force required to press-fit the bushings into the cylindrical core tube and the state of tucking of the end face covers so as to check the state of tucking of the end face covers.

2. The method of checking a wrapping state of a wrapped roll as in claim 1, wherein said sheet material is a photosensitive sheet material.

3. An apparatus for checking a wrapping state of a wrapped roll, the wrapped roll comprising a rolled sheet material which is rolled around a cylindrical core tube and end face covers which cover respective opposite end faces of the rolled sheet material, and wherein portions of the end face covers are tucked into the cylindrical core tube, said apparatus comprising:

pressing-fitting means for press-fitting bushings, having outer diameters smaller than an inner diameter of the cylindrical core tube, in the cylindrical core tube;

press-fitting force detecting means for detecting a press-fitting force transmitted to the press-fitting means from the bushings when press-fitting the bushings in the cylindrical core tube; and determining means for comparing the detected press-fitting force with a predetermined threshold value and for determining whether a tucking of the end face covers is satisfactory as a result of said comparison.

4. An apparatus as defined in claim 3 in which is determined on the basis of a correlation between the force required to press-fit the bushing into the cylindrical core tube and the state of tucking of the end face cover.

5. A method of checking a wrapping state of a wrapped roll, the wrapped roll having a cylindrical core tube with sheet material rolled around the cylindrical core tube and an end face cover which covers an end face of the rolled sheet material, and wherein a portion of the end face cover is tucked into the cylindrical core tube; said method comprising the steps of:

press-fitting a bushing, having an outer diameter smaller than an inner diameter of the cylindrical core tube, in the cylindrical core tube over the tucked portion of the end face cover; and detecting a force required to press-fit the bushing in the cylindrical core tube and comparing the detected force with a threshold value which is determined on the basis of a correlation between the force required to press-fit the bushing into the cylindrical core tube and the state of tucking of the end face cover so as to check the state of tucking of the end face cover.

6. The method of checking a wrapping state of a wrapped roll as in claim 5, wherein said sheet material is a photosensitive sheet material.

7. An apparatus for checking a wrapping state of a wrapped roll, the wrapped roll comprising a rolled sheet material which is rolled around a cylindrical core tube, and an end face cover which covers an end face of the rolled sheet material and wherein a portion of the end face cover is tucked into the cylindrical core tube, said apparatus comprising:

pressing-fitting means for press-fitting a bushing, having an outer diameter smaller than an inner diameter of the cylindrical core tube, in the cylindrical core tube;

press-fitting force detecting means for detecting a press-fitting force transmitted to the press-fitting means from the bushing when press-fitting the bushing in the cylindrical core tube; and determining means for comparing the detected press-fitting force with a predetermined threshold value and for determining whether a tucking of the end face cover is satisfactory as a result of said comparison.

8. The apparatus for checking a wrapping state of a wrapped roll as in claim 7, wherein said rolled sheet material is a photosensitive sheet material.

9. An apparatus for checking a wrapping state of a wrapped roll, the wrapped roll comprising a rolled sheet material which is rolled around a cylindrical core tube and an end face cover which covers an end face of the rolled sheet material, and wherein a portion of the end face cover is tucked into the cylindrical core tube, said apparatus comprising:

a support which supports the wrapped roll;

moveable plates disposed on opposite sides of the support, at least one of said movable plates including a chuck which chucks a bushing having an outer diameter smaller than an inner diameter of the cylindrical core tube;

a drive shaft which relatively moves said movable plates toward each other so as to press-fit the bushing into the cylindrical core tube of the wrapped roll;

a load detector which detects a press-fitting force transmitted to the chuck by the bushing when press-fitting the bushing in the cylindrical core tube; and a comparator which compares the detected press-fitting force with a predetermined threshold value and which determines whether a tucking of the end face cover is satisfactory as a result of said comparison.

10. The apparatus for checking a wrapping state of a wrapped roll as in claim 9, wherein said rolled sheet material is a photosensitive sheet material.

* * * * *